United States Patent [19]

Horn

[11] Patent Number: 4,882,352

[45] Date of Patent: * Nov. 21, 1989

[54] METHOD FOR TREATING SCHIZOPHRENIA

[75] Inventor: Alan S. Horn, Noordorn, Netherlands

[73] Assignee: Nelson Research & Development Co., Irvine, Calif.

[ * ] Notice: The portion of the term of this patent subsequent to Jan. 14, 2003 has been disclaimed.

[21] Appl. No.: 47,882

[22] Filed: May 8, 1987

Related U.S. Application Data

[63] Continuation-in-part of Ser. No. 891,223, Jul. 28, 1986, and a continuation-in-part of Ser. No. 891,262, Jul. 28, 1986, Pat. No. 4,743,618, which is a continuation-in-part of Ser. No. 811,768, Dec. 20, 1985, Pat. No. 4,657,925, which is a continuation-in-part of Ser. No. 640,685, Aug. 13, 1984, Pat. No. 4,564,628, which is a continuation-in-part of Ser. No. 455,144, Jan. 3, 1983, abandoned.

[51] Int. Cl.[4] ............... A61K 31/38; A61K 31/34; A61K 31/42; A61K 31/45
[52] U.S. Cl. .................. 514/438; 514/385; 514/471; 514/443; 514/418; 514/419; 514/415; 514/520; 514/521; 514/522; 514/523; 514/524; 514/525; 514/517; 514/518; 514/319; 514/603; 514/619; 514/649; 514/657
[58] Field of Search ............ 514/357, 471, 438, 385, 514/471, 443, 418, 419, 415, 520, 521, 522, 523, 524, 525, 517, 518, 319, 603, 619, 649, 657

[56] References Cited

U.S. PATENT DOCUMENTS

| | | | |
|---|---|---|---|
| 4,564,628 | 1/1986 | Horn | 514/438 |
| 4,657,925 | 4/1987 | Horn | 514/427 |
| 4,722,933 | 2/1988 | Horn | 549/58 |

Primary Examiner—Alan Siegel
Attorney, Agent, or Firm—Robert J. Baran; June M. Bostich

[57] ABSTRACT

This invention provides a method for treating the symptoms of schizophrenia which comprises administering to a schizophrenic an effective amount of a compound selected from the group consisting of optically-active or racemic compounds represented by the general formula:

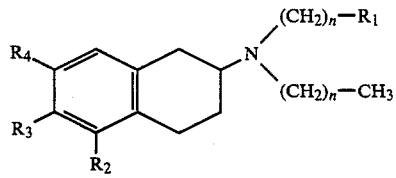

wherein $R_1$ is selected from the group consisting of organic radicals having fused rings, phenyl, pyridyl

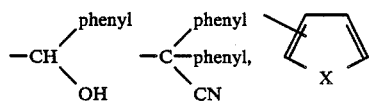

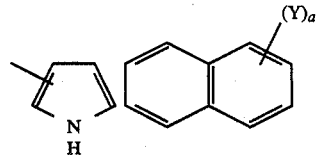

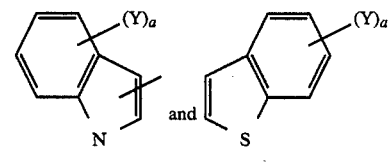

X is oxygen or sulfur, Y, if present, is selected from the group consisting of hydroxy, nitro, cyano, azido, amino, acylamino, carboxyamido, trifluoromethyl, sulfate, sulfonamido halogen, hydrocarbyl and hetero atom-substituted hydrocarbyl radicals, wherein said heteroatoms are selected from the group consisting of halogen, nitrogen, oxygen, sulfur and phosphorus and said hydrocarbyl radicals comprise from 1 to 12 carbon atoms, and a is an integer between zero and 3. $R_2$, $R_3$ and $R_4$ are each selected from the group consising of H and OA, A is H or is selected from the group consisting of hydrocarbyl radicals, or

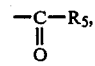

$R_5$ is selected from the group consisting of hydrocarbyl radicals and n is 2 or 3; with the proviso that at least one of $R_2$, $R_3$ and $R_4$ is H, that at least one of $R_2$, $R_3$ and $R_4$ is not H and that $R_2$ and $R_4$ are not both OA, except that when $R_1$ is m-hydroxyphenyl, phenyl or 2-thienyl, the compound is optically-active.

31 Claims, No Drawings

METHOD FOR TREATING SCHIZOPHRENIA

CROSS REFERENCE TO RELATED APPLICATIONS

This patent application is a continuation-in-part of U.S. patent applications Ser. Nos. 891,223 and 891,262 now U.S. Pat. No. 4743618, both filed on July 28, 1986, which applications are continuations-in-part of U.S. patent application Ser. No. 811,768, filed on Dec. 20, 1985 now U.S. Pat. No. 4657925, which is a continuation-in-part of U.S. patent application Ser. No. 640,685, filed on Aug. 13, 1984, now U.S. Pat. No. 4,564,628, which is a continuation-in-part of U.S. patent application Ser. No. 455,144, filed Jan. 3, 1983 and now abandoned. This patent application is also a continuation-in-part of U.S. patent application Ser. No. 839,976, which was filed on Mar. 17, 1986, now U.S. Pat. No. 4722933, which is a continuation-in-part of U.S. patent application Ser. No. 640,685, filed on Aug. 13, 1984, now U.S. Pat. No. 4,564,628, which is a continuation-in-part of U.S. patent application Ser. No. 455,144, filed Jan. 3, 1983 and now abandoned. All of the above applications were filed in the name of Alan S. Horn and are hereby incorporated by reference.

BACKGROUND OF THE INVENTION

1. Field of the Invention

The invention relates generally to substituted 2-aminotetralins useful in treating schizophrenic disorders in humans.

2. Background of the Art

Schizophrenic disorders are mental disorders with a tendency toward chronicity which impairs functioning and which is characterized by psychotic symptoms involving disturbances of thinking, feeling and behavior. Some of the criteria for the diagnosis of a schizophrenic disorder are delusions, hallucinations, formal thought disorder and a deterioration from a previous level of functioning. Schizophrenia specifically excludes organic mental disorders or mental retardation.

Schizophrenia has a worldwide distribution and a lifetime prevelance of 0.2 to 1% as found in studies of Asian and European populations. Higher rates are found in the U.S.A. and U.S.S.R, although the criteria used in these countries are often much broader. Schizophrenia becomes manifest in late adolescence or early adult life. Even with available forms of treatment, schizophrenic patients are said to occupy about half the hospital beds of the mentally ill and mentally retarded patients; and about ¼ of all available hospital beds. Schizophrenia has been found to be found highly prevalent in lower socioeconomical classes which may be attributed to social disorganization and the resulting stresses; but, also there is evidence that this association arises partly because some patients, in a prepsychotic phase, drift down the social scale.

Although schizophrenia is thought to be caused by a complex of both inherited and environmental factors, approximately 10% of the relatives of schizophrenics will be recognized as schizophrenic. Thus, a genetic predisposition is probably necessary, if schizophrenia is to occur at all. The main treatments for schizophrenia are chemotherapeutic, in combination with the development of a therapeutic relationship with a skilled counselor, social support, rehabilitation and retraining. Accepted treatments for schizophrenia include the administration of neuroleptics such as haloperidol, chlorpromazine or thioridazine delivered parenterally or orally. The most widely accepted theory of the mode of action of these compounds is that they block dopamine receptor sites in the CNS (Seeman, Pharmacol. Rev. 32 229313, 1980) Other drugs of choice for the biochemical therapy of schizophrenia include butyrophenones, thioxanthenes, dihydroindolones and dibenzoxazepines.

Recently, many patents have issued disclosing the use of different chemical entities for treatment of schizophrenia. For example, in U.S. Pat. No. 4,577,020 certain aminoalkyl and aminoalkenyl triazoles are disclosed as useful antipsychotic drugs. In U.S. Pat. No. 4,588,721 a process for preventing the negative symptoms of schizophrenia is disclosed, which utilizes, as the active agent, a class of compounds which may be defined as benzodiazepines. U.S. Pat. No. 4,593,041 utilizes benzopyrone-type drugs for the treatment of schizophrenia. U.S. Pat. No. 4,626,549 suggests that certain 3-aryloxy-3-phenylpropyl-amines may be used in the treatment of schizophrenia. Finally, U.S. Pat. No. 4,620,977 discloses that certain N,N-dimethylated indolamines, are useful for the treatment of schizophrenia.

While there are many theories as to the neurochemical nature of the illness, it is thought by some researchers that schizophrenia results from a hyperactivity of dopamine-containing neurons in certain areas of the brain. Recently it has been suggested that a new approach to the treatment of schizophrenia could possibly be achieved by selectively stimulating dopamine autoreceptors (which control dopamine synthesis and release and are of the $D_2$ type) rather than blocking postsynaptic dopamine receptors with the classical neuroleptics (Meltzer, Schiz. Bulln., 6 456–475, 1980). It has also been reasoned that this could lead to fewer CNS-related side effects.

In the case of two dopamine agonists, i.e. apomorphine and N-propylnorapomorphine, clinical studies have tended to support the above proposal (Tamminga et al., Science, 200 567–568, 1978, Tamminga et al., Arch. Gen. Psy. 43, 398–402. Thus, there is this extensive interest in discovering new dopamine agonists which have a selective action on dopamine autoreceptors. See also J. C. Van Oene et al, European Journal of Pharmacology, 87 (1983), pgs. 491–495 and J. C. Van Oene et al, European Journal of Pharmacology, 102 (1984), pgs. 101–115 and Annual Reports in Medicinal Chemistry—20, Chapter 5, entitled "Dopamine Receptors and Dopaminergic Agents" by Schaus et al.

Thus, it is clear from the above that the search for chemical agents or drugs useful for the treatment of schizophrenia is continuing.

SUMMARY OF THE INVENTION

The present invention provides a method for treating the symptoms of schizophrenia which comprises administering to a schizophrenic an effective amount of a compound selected from the group consisting of optically-active or racemic compounds represented by the general formula:

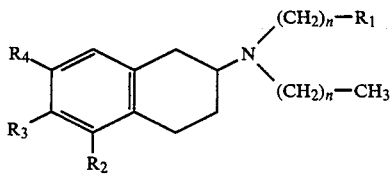

wherein R₁ is selected from the group consisting of organic radicals having fused rings, phenyl, pyridyl

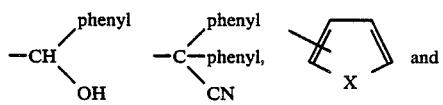

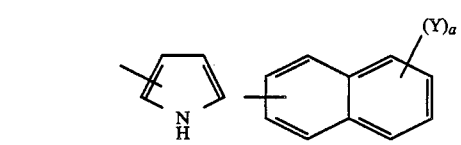

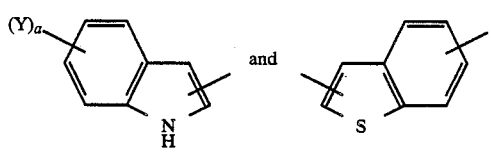

X is oxygen or sulfur, Y, if present, is selected from the group consisting of atoms, and a is an integer between zero and 3. and further substituted derivatives thereof wherein any of the aromatic rings may be substituted with hydroxy, nitro, cyano, azido, amino, acylamino, carboxyamido, trifluoromethyl, sulfate, sulfonamido, halogen, hydrocarbyl and hetero atom-substituted hydrocarbyl radicals, wherein said heteroatoms are selected from the group consisting of halogen, nitrogen, oxygen, sulfur and phosphorus and said hydrocarbyl radicals comprise from 1 to 12 carbon atoms.

R₂, R₃ and R₄ are each selected from the group consisting of H and OA; A is H or is selected from the group consisting of hydrocarbyl radicals, or

R₅ is selected from the group consisting of hydrocarbyl radicals and n is 2 or 3; with the proviso that at least one of R₂, R₃ and R₄ is H, that at least one of R₂, R₃ and R₄ is not H and that R₂ and R₄ are not both OA except that when R₁ is m-hydroxyphenyl, phenyl or 2-thienyl the compound is optically active.

In the method of the present invention it is preferred that said radicals are not further substituted.

A is preferably H or is selected from the group consisting of phenyl and alkyl radicals having from 1 to 12 carbon atoms, and more preferably A is an alkyl radical having from 1 to 3 carbon atoms.

The more preferred groups represented by R₁ are thienyl, phenyl, hydroxyphenyl, furanyl and naphthalenyl, e.g. 2-thienyl, 3-thienyl, 3-hydroxyphenyl, 4-hydroxyphenyl, etc.

In the more preferred compounds for use in the present invention n is 2 and R₂, R₃ and R₄ are selected from the group consisting of H and

e.g. R₄ and R₃ may be H.

Finally, it is even more preferred that the compound selected for use in the method of the present invention be an optically active compound capable of activating the presynaptic D₂ dopamine receptor, e.g. in a human, without substantially actuating postsynaptic dopamine receptors. In particular, it is found that the dextro (plus) enantiomer of 5-hydroxy-2-(N-n-propyl-N-[2-thienyl-]ethyl-amino)tetralin is especially preferred for use in the method of the present invention.

DETAILED DESCRIPTION OF THE INVENTION

Compounds useful in the method of the present invention may be made by the methods disclosed in the above cited patent applications which are hereby incorporated by reference hereto. Particularly preferred compounds are as follows:

Compounds wherein R₁ is an organic radical comprising a fused ring wherein R₁ is selected from the group of radicals represented by the general formulae:

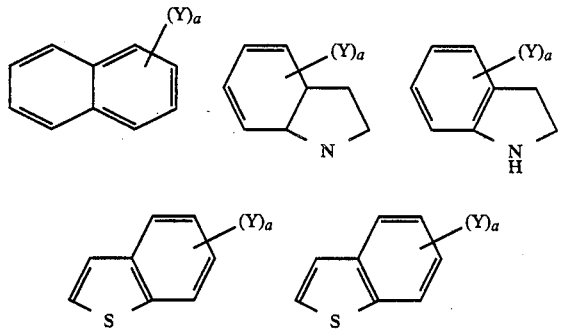

wherein Y is selected from the group consisting of hydroxy, nitro, cyano, azido, amino, trifluoromethyl, halogen, acylamino, carboxamido, sulfonamido, hydrocarbyl and heteroatom-substituted hydrocarbyl radicals; wherein said heteroatoms are selected from the group consisting of halogen, nitrogen, oxygen, sulfur and phosphorus and said hydrocarbyl radicals comprise from 1 to 12 carbon atoms and a is an integer of from 0 to 3. (R₁ may be covalently bonded to the nitrogen atom, through —(CH₂)ₙ—, at any position on either of the fused rings.) More preferably, Y comprises no more than 5 carbon atoms and a is 0 or 1. Specific preferred compounds of this group include:

2-(N-n-propyl-N-2-[naphthalenyl]ethylamino)-5-hydroxytetralin, 2-(N-n-propyl-N-2-[4-indolyl]ethylamino)-5-hydroxytetralin, 2-(N-n-propyl-N-2-[benzothienyl]ethylamino)-5-hydroxy-tetralin, and 2-(N-n-propyl-N-3-[benzothienyl]ethylamino-5-hydroxy-tetralin;

Compounds wherein R₁ is phenyl and/or substituted phenyl and is selected from the group of radicals represented by the general formula:

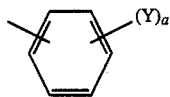

wherein Y and a are as defined above. Specific preferred compounds of this group include:

2-(N-n-propyl-N-2-[phenyl]ethylamino)-5-hydroxytetralin, 2-(N-n-propyl-N-2-[4-hydroxyphenyl]ethylamino)-5-hydroxyteralin, and 2-(N-n-propyl-N-2-[3-hydroxyphenyl]ethylamino)-5-hydroxytetralin;

Compounds wherein $R_1$ is selected from the group consisting of radicals represented by the general forumla:

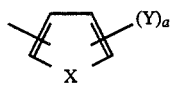

wherein X, Y and a are as defined above. Specific preferred compounds of this group include:

2-(N-n-propyl-N-2-[2-thienyl]ethylamino)-5-hydroxytetralin, 2-(N-n-propyl-N-2-[3-thienyl]ethylamino)-5-hydroxytetralin, 2-(N-n-propyl-N-2-[2-furanyl]ethylamino)-5-hydroxytetralin, 2-(N-n-propyl-N-2-[3-furanyl]ethylamino)-5-hydroxytetralin, 2-(N-n-propyl-N-2-[2-thienyl-4-methyl]ethylamino)-5-hydroxytetralin, 2-(N-n-propyl-N-2-[2-thienyl-3,4,5-trimethyl]ethylamino-5-hydroxytetralin, 2-(N-n-propyl-N-2-[2-thienyl-5-chloro]ethylamino)-5-hydroxytetralin, 2-(N-n-propyl-N-2-[2-thienyl-4-bromo-5-methyl]ethylamino)-5-hydroxytetralin, 2-(N-n-propyl-N-2-[2-thienyl-4-methyl-5-ethyl]ethylamino-5-hydroxytetralin, 2-(N-n-propyl-N-2-[3-benzothienyl]ethylamino)-5-hydroxytetralin and 2-(N-n-propyl-N-2-[3-benzothienyl]ethylamino)-5-hydroxytetralin.

This invention provides a method of treatment which comprises inducing a response at the $D_2$ dopamine autoreceptors which control the synthesis and release of dopamine in the brain of a schizophrenic patient by administering a therapeutically effective amount of one of the foregoing compounds to the patient. In general, a pharmacologically-effective daily dose can be from 0.01 mg./kg. to 100 mg./kg. per day, and preferably from about 0.1 mg./kg. to 25 mg./kg. per day, bearing in mind, of course, that in selecting the appropriate dosage, in any specific case, consideration must be given to the patient's weight, general health, metabolism, age and other factors which influence response to the drug. A particularly preferred dose is 1.0 mg./kg. per day.

Another embodiment of this invention is the provision of pharmaceutical compositions in dosage unit form which comprise from about 2 mg. to 500 mg. of a compound of the above formula.

The pharmaceutical composition may be in a form suitable for oral use, for example, as tablets, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents, and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, for example calcium carbonate, sodium carbonate, lactose, calcium phosphate, or sodium phosphate; granulating and disintegrating agents, for example maize starch, or alginic acid; binding agents, for example starch, gelatine, or acacia; and lubricating agents, for example magnesium stearate, stearic acids, or talc. The tablets may be uncoated or they may be coated by known techniques to delay disintegration and adsorption in the gastrointestinal tract and thereby provide a sustained action over a longer period.

Formulations for oral use may also be presented as hard gelatine capsules wherein the active ingredient is mixed with an inert solid diluent, for example calcium carbonate, calcium phosphate, or kaolin, or as soft gelatine capsules wherein the active ingredient is mixed with an oil medium, for example arachis oil, liquid paraffin, or olive oil.

Aqueous suspensions contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth, and gun acacia; dispersing or wetting agents may be naturally-occurring phosphatides, for example lecithin, or condensation products of an alkylene oxide with fatty acids, for example polyoxethylene stearate, or condensation products of ethylene oxide with long chain aliphatic alcohols, for example heptadecethyleneoxycetanol, or condensation products of ethylene oxide with partial esters derived from fatty acids and a hexitol, for example, polyoxyethylene sorbitol monooleate, or condensation products of ethylene oxide with partial esters derived from fatty acids and hexitol anhydrides, for example polyoxyethylene sorbitan monooleate. The aqueous suspensions may also contain one or more preservatives, for example ethyl, n-propyl, or p-hydroxy benzoate, one or more coloring agents, one or more flavoring agents and one or more sweetening agents, such as sucrose, saccharin, or sodium or calcium cyclamate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents may also be present.

Syrups and elixirs may be formulated with sweetening agents, for example glycerol, sorbitol or sucrose. Such formulations may also contain a demulcent, preservative, flavoring and coloring agents. The pharmaceutical compositions may be in the form of a sterile injectable preparation, for example as a sterile injectable aqueous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol.

The pharmaceutical compositions may be tableted or otherwise formulated so that for every 100 parts by weight of the composition there are present between 5 and 95 parts by weight of the active ingredient. The dosage unit form will generally contain between about 1 mg. and about 100 mg. of the active ingredient of the formula stated above.

From the foregoing formulation discussion it is apparent that the compositions of this invention can be administered orally or parenterally. The term parenteral as used herein includes subcutaneous injection, intravenous, intramuscular, or intrasternal injection or fusion techniques. The compositions can also be administered ransdermally with the use of an appropriate transdermal vehicle, as described in U.S. Pat. No. 4,405,616. The preferred vehicle is 1-n-dodecylazacycloheptan-2-one.

To illustrate the manner in which the invention may be carried out, the following examples are given. It is understood, however, that the examples are for the purpose of illustration and the invention is not to be regarded as limited to any of the specific materials or conditions therein.

EXAMPLE

Animal test models for either presynaptic or postsynaptic dopaminergic receptor function in the central nervous system were used to compare the effects of the (+) and (−) stereoisomers of 2-N-n-propyl-N-2-[2-thienyl]ethylamino)-5-hydroxytetralin (N-0437). It is believed that it is desirable for the treatment of schizophrenia, that the dopaminergic agent activate the presynaptic or auto receptors. (See for example, Tamminga et al., SCIENCE, Vol. 200, 5 May 1978 at pp. 567–8 and Meltzer et al., Psychopharmacology (1983) 81:37-41.)

Presynaptic Dopamine Receptor Activity

γ-Butyrolactone (GBL) Model

γ-Butyrolactone (GBL), (8.7 mmol/kg, i.p.) induces a marked increase in dopamine synthesis in the striatum and olafactory tubercle of the rat brain. The ability of a drug to prevent the increased dopamine synthesis in this model is considered an index of the drug's direct effect on presynaptic terminals of dopaminergic neurons (Walters, J. R. and Roth, R. H., 1976, Naunyn-Schmiedels Arch. Pharmacol., 296:5–14).

The method of Van der Weide et al (1986, Eur. J. Pharmacology, 125:273–282) was used. Each test drug was administered, i.p. to 4–5 rats, five minutes prior to GBL injection. Dopamine synthesis in the striatum and olafactory tubercle was determined by measuring dihydroxyphenylalanine levels following decarboxylase inhibition with 3-hydroxybenzylhydrazine 2 HCl (0.47 mol/kg, i.p.). Log dose—effect curves were used to calculate the $ED_{50}$ and $ED_{100}$, i.e. the dose which reverses the GBL effect by 50% or 100%, respectively. Results with (+) N-0437 and (−) N-0437 are given in Table 1.

TABLE 1

|  | Striatum $ED_{50}(\mu mol/kg)$ | Olefactory Tubercle $ED_{100}$ ($\mu mol/kg$) |
| --- | --- | --- |
| (+) N-0437 | 0.18 | 0.22 |
| (−) N-0437 | 0.13 | 0.20 |
| apomorphine | 1.1 | 1.7 |

Both steroisomers of N-0437 were similarly effective as agonists in this in vivo model for presynaptic dopamine receptors. Both were more potent than the reference dopamine agonist, apomorphine.

Inhibition of Spontaneous Locomotor Activity in Mice

Inhibition of spontaneous locomotor activity in rodents by dopamine agonists is thought to be mediated via dopamine autoreceptors (Martin, G. E. and Bendesky, R. J., 1984, J. Pharmacol. Exp. Ther. 229:706–711).

The procedure used for this test was that of Hazelhoff, B. et al, 1986, Eur. J. Pharmacol 124:93–106. Drugs were injected i.p. into female Swiss mice, and five minutes later, the animals were placed into a rectangular activity case where locomotor activity was measured with a Automex motility meter.

The results with 10 μmol/kg of (+) N-0437 and (−) N-0437 and a racemic mixture of (±) N-0437 are given in Table 2.

TABLE 2

|  | Activity Counts/30 Min. |
| --- | --- |
| Control | 2236 ± 93 (10) |
| (+) N-0437 (Saline) | 470 ± 74 (6) |
| (−) N-0437 | 660 ± 82 (6) |
| (±) N-0437 | 449 ± 82 (6) |

Both stereoisomers of N-0437 were similarly effective in the mouse locomotor activity model for dopamine autoreceptor activator.

Postsynatic Dopamine Receptor Activity

Stereotyped Behavior in rats

Stereotyped behaviors such as continuous gnawing, biting, licking, are observed following stimulation of postsynatic dopamine receptors. (Ernst, A. M., 1967, Psychopharmacologia, 10:316). The method of van der Weide, J. et al (1986, Eu. J. Parmacol., 125:273–282) was used to assess the intensity of stereotyped behavior in male rats injected i.p. with either (−) N-0437 or (+) N-0437. (−) N-0437 produced a half maximal effect at 1.7 μmol/kg. However, (+) N-0437 was inactive in this test for postsynaptic dopamine receptor activity at doses up to 100 μg/kg.

Turning behavior in 6-hydroxydopamine lesioned rats

Dopamine agonists produce contralateral circling behavior in rats which unilateral lesions of the substantia nigra which are made by prior injection of 6-hydroxy dopamine. The circling is thought to be mediated by stimulation of devernated supersensitive postsynaptic dopamine receptors (Marshall and Ungerstedt, 1977, Eur. J. Pharmacol., 41:361-367). The method of Van der Werf, et al (1984), Eur. J. Pharmacol. 102:387–399) was used. (−) N-0437, (+) N-0437 and (±) N-0437 (racemic mixture) were administered at a dose of 1 μmol/kg, i.p., and the animals were placed immediately into automated rotometers.

| | No. of turns/30 min. |
|---|---|
| (−) N-0437 | 278 ± 39 (4) |
| (+) N-0437 | 0 ± 5 (4) |
| (±) N-0437 | 171 ± 32 (4) |

(−) N-0437 showed significant activity in this postsynaptic dopamine receptor model while (+) N-0437 showed no effect.

In view of the above, it is clear that the presynaptic $D_2$ dopamine receptors may be activated without appreciably activating postsynaptic dopamine receptors. This discovery may enable one to treat the symptoms of schizophrenia without causing the side effects associated with the interaction of the dopaminergic agent with the postsynaptic dopamine receptors.

While particular embodiments of the invention have been described, it will be understood, of course, that the invention is not limited thereto since many obvious modifications can be made and it is intended to include within this invention any such modifications as will fall within the scope of the appended claims. For example, this invention may be used to treat other diseases that are believed to involve an enhanced functioning of central dopaminergic neurons, e.g. Huntington's chorea, Tourette's syndrome and mania.

Having now described the invention, I claim.

1. A method for treating the symptoms of schizophrenia comprising activating the presynaptic $D_2$ dopamine receptors without substantially activating the postsynaptic receptors by administering to a schizophrenic an effective amount of a compound consisting essentially of the dextro (plus) isomers of compounds selected from the group represented by the general formula:

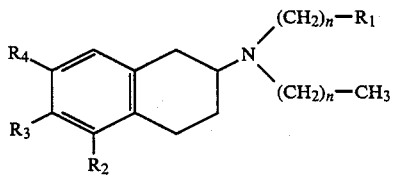

wherein $R_1$ is selected from the group consisting of phenyl, pyridyl

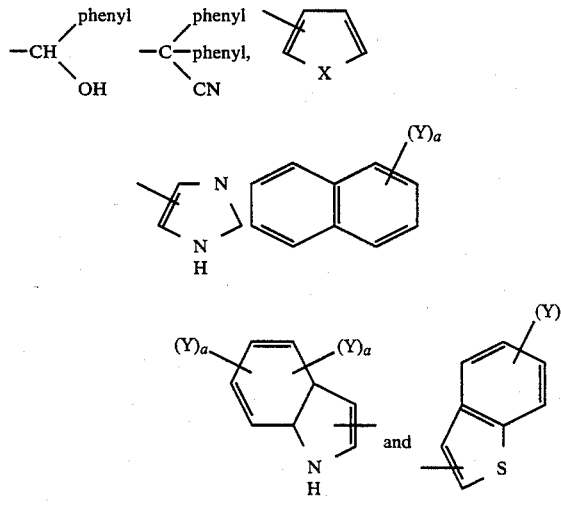

X is oxygen or sulfur, Y, if present, is selected from the group consisting of hydroxy, nitro, cyano, azido, amino, acylamino, carboxyamido, trifluoromethyl, sulfate, sulfonamido, halogen, hydrocarbyl and hetero atom-substituted hydrocarbyl radicals, wherein said heteroatoms are selected from the group consisting of halogen, nitrogen, oxygen, sulfur and phosphorus and said hydrocarbyl radicals comprise from 1 to 12 carbon atoms, and a is an integer between zero and 3, $R_2$, $R_3$ and $R_4$ are each selected from the group consisting of H and OA, A is H or is selected from the group consisting of hydrocarbyl radicals, or

$R_5$ is selected from the group consisting of hydrocarbyl radicals and n is 2 or 3; with the proviso that at least one of $R_2$, $R_3$ and $R_4$ is H, that at least one of $R_2$, $R_3$ and $R_4$ is not H and that $R_2$ and $R_4$ are not both OA.

2. The method of claim 1 wherein a is zero and $R_2$ is OA and A is H.

3. The method of claim 2 wherein A is selected from the group consisting of phenyl and alkyl radicals having from 1 to 12 carbon atoms.

4. The method of claim 3 wherein A is selected from alkyl radicals having from 1 to 3 carbon atoms.

5. The method of claim 4 wherein $R_1$ is selected from the group consisting of thienyl, phenyl, hydroxyphenyl, furanyl and naphthalenyl.

6. The method of claim 5 wherein n is 2.

7. The method of claim 6 wherein $R_2$, $R_3$ and $R_4$ are selected from the group consisting of H and

8. The method of claim 7 wherein said $R_1$ is selected from the group consisting of 2-thienyl and 3-thienyl.

9. The method of claim 8 wherein $R_4$ and $R_3$ are H.

10. The method of claim 9 wherein $R_1$ is 2-thienyl.

11. The method of activating the presynaptic $D_2$ dopamine receptors of a human, without appreciably activating postsynaptic dopamine receptors, comprising administering to said human an effective amount of a compound consisting essentially of the dextro (plus) isomers of compounds represented by the general formula:

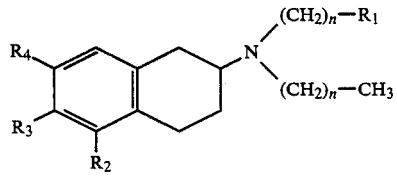

wherein $R_1$ is selected from the group consisting of phenyl, pyridyl

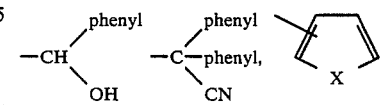

-continued

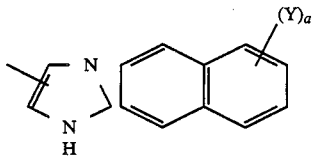

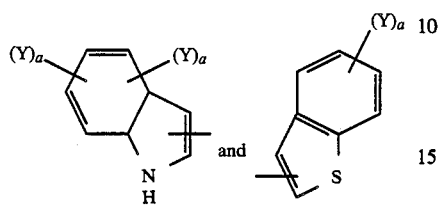

X is oxygen or sulfur, Y, if present, is selected from the group consisting of hydroxy, nitro, cyano, azido, amino, acylamino, carboxyamido, trifluoromethyl, sulfate, sulfonamido, halogen, hydrocarbyl and hetero atom-substituted hydrocarbyl radicals, wherein said heteroatoms are selected from the group consisting of halogen, nitrogen, oxygen, sulfur and phosphorus and said hydrocarbyl radicals comprise from 1 to 12 carbon atoms, and a is an integer between zero and 3, $R_2$, $R_3$ and $R_4$ are each selected from the group consisting of H and OA, A is H or is selected from the group consisting of hydrocarbyl radicals, or

$R_5$ is selected from the group consisting of hydrocarbyl radical and n is 2 or 3; with the proviso that at least one of $R_2$, $R_3$ and $R_4$ is H, that at least one of $R_2$, $R_3$ and $R_4$ is not H and that $R_2$ and $R_4$ are not both OA.

12. The method of claim 11 wherein a is 0 and $R_2$ is OA and A is H.

13. The method of claim 12 wherein A is selected from the group consisting of phenyl and alkyl radicals having from 1 to 12 carbon atoms.

14. The method of claim 13 wherein A is selected from alkyl radicals having from 1 to 3 carbon atoms.

15. The method of claim 14 wherein $R_1$ is selected from the group consisting of thienyl, phenyl, hydroxyphenyl, furanyl and naphthalenyl.

16. The method of claim 15 wherein n is 2.

17. The method of claim 16 wherein $R_2$, $R_3$ and $R_4$ are selected from the group consisting of H and

18. The method of claim 17 wherein said $R_1$ is selected from the group consisting of 2-thienyl and 3-thienyl.

19. The method of claim 18 wherein $R_4$ and $R_3$ are H.

20. The method of claim 19 wherein $R_1$ is 2-thienyl.

21. The method of claim 20 wherein the compound is the dextro (plus) enantiomer of 5-hydroxy-2-(N-n-propyl-N-[2-thienyl]ethyl)-aminotetralin.

22. A method for treating the symptoms of diseases involving the enhanced functioning of presynaptic dopaminergic $D_2$ receptors without appreciably activating postsynaptic dopamine receptors which comprises administering to a patient suffering the disease an effective amount of a compound consisting essentially of the dextro (plus) isomers of compounds represented by the general formula:

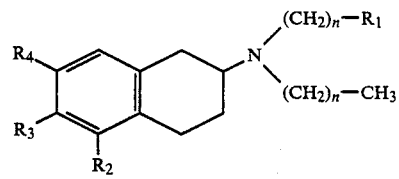

wherein $R_1$ is selected from the group consisting of phenyl, pyridyl

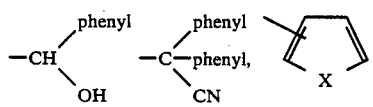

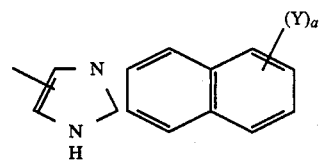

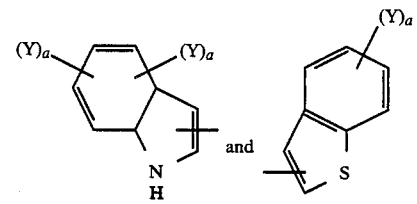

X is oxygen or sulfur, Y, if present, is selected form the group consisting of hydroxy, nitro, cyano, azido, amino acylamino, carboxyamido, trifluoromethyl, sulfate, sulfonamido, halogen, hydrocarbyl and hetero atom-substituted hydrocarbyl radicals, wherein said heteroatoms are selected from the group consisting of halogen, nitrogen, oxygen, sulfur and phosphorus and said hydrocarbyl radicals comprise from 1 to 12 carbon atoms, and a is an integer between zero and 3.

$R_2$, $R_3$ and $R_4$ are each selected from the group consisting of H and OA, A is H or is selected from the group consisting of hydrocarbyl radicals, or $$-\overset{\overset{\displaystyle O}{\|}}{C}-R_5,$$

$R_5$ is selected from the group consisting of hydrocarbyl radical and n is 2 or 3; with the proviso that at least one of $R_2$, $R_3$ and $R_4$ is H, that at least one of $R_2$, $R_3$ and $R_4$ is not H and that $R_2$ and $R_4$ are not both OA 23. The method of claim 22 wherein said y is equal to zero and $R_2$ is OA and A is H.

24. The method of claim 23 wherein A is selected from the group consisting of phenyl and alkyl radicals having from 1 to 12 carbon atoms.

25. The method of claim 24 wherein A is selected from alkyl radicals having from 1 to 3 carbon atoms.

26. The method of claim 25 wherein $R_1$ is selected from the group consisting of thienyl, phenyl, hydroxyphenyl, furanyl and naphthalenyl.

27. The method of claim 26 wherein n is 2.

28. The method of claim 27 wherein $R_2$, $R_3$ and $R_4$ are selected from the group consisting of H and

29. The method of claim 28 wherein said $R_1$ is selected from the group consisting of 2-thienyl and 3-thienyl.

30. The method of claim 29 wherein $R_4$ and $R_3$ are H.

31. The method of claim 30 wherein $R_1$ is 2-thienyl.

* * * * *